United States Patent [19]

Buser et al.

[11] Patent Number: 4,848,894
[45] Date of Patent: Jul. 18, 1989

[54] CONTACT LENS WITH LASER PROTECTION

[75] Inventors: Rudolph G. Buser, Wall, N.J.; C. Ward Trussell, Woodbridge, Va.

[73] Assignee: The United States of America as represented by the Secretary of the Army, Washington, D.C.

[21] Appl. No.: 200,990

[22] Filed: Jun. 1, 1988

[51] Int. Cl.$^4$ .................. G02C 7/10; G02C 7/04; G02B 5/28; G02B 5/32
[52] U.S. Cl. .................. 351/162; 350/3.72; 350/166
[58] Field of Search ............. 351/160 H, 160 R, 161, 351/162, 163; 350/163, 164, 165, 166, 3.7, 3.72

[56] References Cited

U.S. PATENT DOCUMENTS

| | | | |
|---|---|---|---|
| 3,519,339 | 7/1970 | Hutchinson et al. | 351/163 X |
| 3,701,590 | 10/1972 | Zeltzer | 351/162 X |
| 3,877,797 | 4/1975 | Thornton, Jr. | 351/163 X |
| 4,637,697 | 1/1987 | Freeman | 351/177 X |

FOREIGN PATENT DOCUMENTS 2445794  4/1976  Fed. Rep. of Germany ...... 351/163

Primary Examiner—Rodney B. Bovernick
Assistant Examiner—Scott J. Sugarman
Attorney, Agent, or Firm—Milton W. Lee; Aubrey J. Dunn; Anthony T. Lane

[57] ABSTRACT

A contact lens is made either with a laser-reflecting or absorbing layer embedded in a transparent optical lens material, or formed as a layer on the convex side of such a material. The layer may be a Fabry-Perot reflector or a thin-film or holographically formed reflective or absorptive interference filter, or an absorbing layer.

8 Claims, 1 Drawing Sheet

CONTACT LENS WITH LASER PROTECTION

The invention described herein may be manufactured, used, and licensed by the U.S. Government for governmental purposes without the payment of any royalties thereon.

BACKGROUND OF THE INVENTION

This invention is in the field of protectors for eyes against intense optical radiation. More particularly, it is concerned with protecting eyes against laser radiation. There are many known ways of and schemes for protecting the eyes against intense optical radiation: perhaps the best known example is sun glasses. Another well-known example is welder's goggles. Various shutter devices, both mechanical and electro-optical have been proposed. With the invention of the laser, a new threat to the eyes was created. All of the above-mentioned ways of protecting the eyes have also been usable to some extent against some lasers. With the advent of high-power and rapid rise-time and tunable lasers however, most of the known protective techniques proved inadequate. This has led to the development of such things as spectacles having lenses covered by optical interference filters or Fabry-Perot reflectors, or having lenses or lens coating formed of non-linear optical materials. The non-linear materials may have optical densities dependent on intensity (or power) of incident radiation (photochromic materials). Many of the means now known for protecting eyes against laser radiation work quite well for their intended purpose. They do however, have certain disadvantages. Specifically, when worn as spectacles or goggles, all such means have limited fields of view or angles of protection (or both). Moreover, like all spectacles and goggles, they may be uncomfortable when worn for long periods, will interfere with the use of optical devices such as telescopes, and must be stored and protected when not in use. The instant invention overcomes these disadvantages by being in the form of contact lenses. Although tinted and optically dense contact lenses are known, such lenses are not intended as protectors of the eyes against laser radiation, but are used for cosmetic purposes or as sun glasses. Also known are contact lenses which protect the eyes against ultraviolet radiation; these act by absorbing incident ultraviolet radiation (contact lens sun glasses also operate by absorption).

SUMMARY OF THE INVENTION

The invention is a contact lens for protecting the human eye against high-power or high-intensity optical radiation such as that from a laser. The lens has a concave side contoured to fit on the cornea of the eye and a protective layer either internal to the lens or on the convex side. The protective layer may be a Fabry-Perot reflector, a thin-film interference filter, or a holographic filter, such that laster radiation is absorbed or reflected by the lens. Alternatively, the lens may be formed of a material which is or which contains a narrow-band absorber.

DESCRIPTION OF PREFERRED EMBODIMENTS

Figure 1:
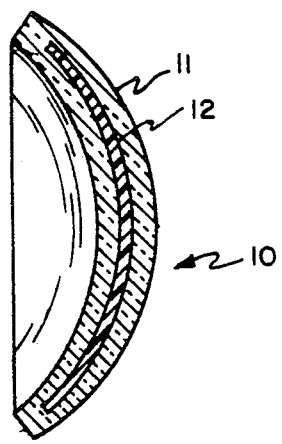
FIG. 1 is a side cross-sectional view of one embodiment of the invention.

This invention may be best understood when this description is taken in conjunction with the drawings. In FIG. 1, we see an embodiment of the invention wherein a contact lens generally designated 10 consists of a transparent material 11 with layer 12 imbedded in 11. Material 11 is the usual material from which contact lenses are made, and may be glass or hard or soft plastic. Lens 10 is contoured in the usual manner on its concave side with a particular radius of curvature to fit the cornea of the wearer's eye, and its convex side may be the same radius of curvature (but different sign) if a plano lens is desired (no diopter correction). Obviously, if correction is needed for the wearer, the lens may be made to provide such correction. Layer 12 may taken any one of several forms, and is where protection of the eye occurs; the forms include optical interference filters such as thin-film types, Fabry-Perot reflectors, and halographic filters. Whatever form, the layer must be highly reflective to laser radiation. In the case in which glass is used for material 11, layer 12 must be made of materials capable of withstanding molten glass temperatures, or 12 may be cemented between two properly formed lens elements.

Figure 2:
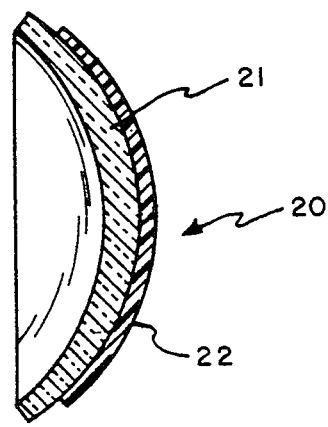
FIG. 2 is a side cross-sectional view of another embodiment of the invention.

FIG. 2 varies from FIG. 1 in that lens 20 consists of transparent material 21 with a laser-reflecting layer 22 on its convex side. Layer 22 may take any one of the forms as mentioned above for layer 12, and may be formed directly onto material 21, or made elsewhere and applied to 21.

Figure 3:
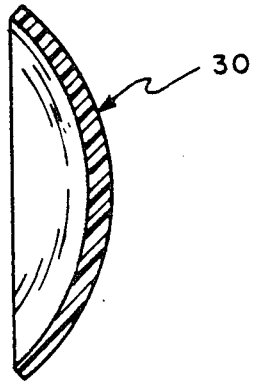
FIG. 3 is a side cross-sectional view of yet another embodiment of the invention.

FIG. 3 is an embodiment of the invention wherein the lens 30 is formed of a laser-radiation absorbing material. Ideally, the material should be very narrow-band (in accordance with the wavelength of an expected threat laser) to avoid blocking out non-threatening radiation. The lens may be made of an acrylic plastic or other plastic material with absorptive dyes distributed uniformly throughout the material. Examples of such dyes are various metalloporphyrins and derivatives of phthalocyanine. Alternatively, the absorbing materials may be deposited as a surface layer on a glass or plastic lens substrate, or may be made as a layer with the lens, as discussed above in the description of the FIG. 1 embodiment.

One might wonder whether an absorbing lens would heat up when subjected to laser radiation and cause searing of the cornea on which it is carried. This is not a significant concern; laser radiation capable of doing damage to the eye may contain so little energy that it would cause an infinitesimal temperature rise when absorbed by 30, but may have such a high peak power that it could harm the eye. Even peak powers which cause no damage to the cornea of the eye may, because of focussing by the lens of the eye, cause severe damage to the retina.

In some cases, it may be desirable to combine one or more of the techniques of FIGS. 1-3, in order to obtain greater protection against threat lasers. Obviously, the techniques may also be combined to protect against multiple, i.e., different wavelength lasers, or a particular technique may be fabricated to so protect.

With the above description, we have set forth a device which provides protection against high-power or high-energy laser radiation, but which avoids the problems of laser-protection spectacles. Specifically, the contact lenses of this invention provide their protection without interfering with other optical devices which the wearer may use, such as telescopes, have a wide field of view compared to spectacles, and provide protection from essentially all directions of incident laser radiation. In addition to the various materials and layers described above, some of which are wavelength-sensitive, a broadband non-linear optical material may be used to advantage. Such a material is essentially transparent to a broad band of radiation below some intensity or power threshold level, but undergoes a dramatic change in some optical property (such as optical density) for radiation above the threshold level. A material which undergoes such an optical density changes thus acts as an absorber for high-intensity or high-power radiation. Examples of such materials are those shown in U.S. Pat. No. 3,620,597.

We claim:

1. A contact lens for placement on the cornea of the human eye and for protecting said eye against high-intensity or high-power incident optical radiation of a particular wavelength or wavelengths and consisting of:

an optically transparent material formed with a concave side conforming to the contour of the cornea of a human eye, and with a convex side, an optical interference filter on said convex side for said particular wavelength or wavelengths of incident radiation, whereby substantially all wavelengths but said particular wavelength or wavelengths are transmitted by said lens and said particular wavelength or wavelengths are absorbed or reflected thereby.

2. The lens as set forth in claim 1 wherein said interference filter is a thin-film type.

3. The lens as set forth in claim 1 wherein said interference filter is holographically formed.

4. A contact lens for placement on the cornea of the human eye and for protecting said eye against high-intensity or high-power incident optical radiation of a particular wavelength or wavelengths and consisting of:

an optically transparent material formed with a concave side conforming to the contour of the cornea of a human eye, and with a convex side, and an optical Fabry-Perot reflector on said convex side for said particular wavelength or wavelengths of incident radiation, whereby substantially all wavelengths but said particular wavelength or wavelengths are transmitted by said lens and said particular wavelength or wavelengths are reflected thereby.

5. A contact lens for placement on the cornea of the human eye and for protecting said eye against high-intensity or high-power incident optical radiation of a particular wavelength or wavelengths consisting of:

an optically transparent material formed with a concave side conforming to the contour of the cornea of a human eye, and with a convex side, and an optical interference filter formed within said transparent material as a layer substantially parallel to the sides of the material, for said particular wavelength or wavelengths of incident radiation, whereby substantially all wavelengths but said particular wavelength or wave-lengths are transmitted by said lens and said particular wavelength or wavelengths are absorbed or reflected thereby.

6. The lens as set forth in claim 5 wherein said interference filter is a thin-film type.

7. The lens as set forth in claim 5 wherein said interference filter is holographically formed.

8. A contact lens for placement on the cornea of the human eye and for protecting said eye against high-intensity or high-power incident optical radiation of a particular wavelength or wavelengths and consisting of:

an optically transparent material formed with a concave side conforming to the contour of the cornea of a human eye, and with a convex side, and a Fabry-Perot reflector formed within said transparent material as a layer substantially parallel to the sides of the material, for said particular wavelength or wavelengths of incident radiation, whereby substantially all wavelengths but said particular wavelength or wavelengths are transmitted by said lens and said particular wavelength or wavelengths are reflected thereby.

* * * * *